(12) United States Patent
Baaijens et al.

(10) Patent No.: US 11,089,665 B2
(45) Date of Patent: Aug. 10, 2021

(54) LIGHTING SYSTEM AND A LIGHTING METHOD

(71) Applicant: SIGNIFY HOLDING B.V., Eindhoven (NL)

(72) Inventors: Johannes Petrus Wilhelmus Baaijens, Eindhoven (NL); Joanne Henriette Desiree Monique Westerink, Eindhoven (NL); Luca Tiberi, Eindhoven (NL); Maurice Herman Johan Draaijer, Ittervoort (NL); Ralf Gertruda Hubertus Voncken, Eindhoven (NL)

(73) Assignee: Signify Holding B.V., Eindhoven (NL)

( * ) Notice: Subject to any disclaimer, the term of this patent is extended or adjusted under 35 U.S.C. 154(b) by 430 days.

(21) Appl. No.: 16/062,746

(22) PCT Filed: Dec. 6, 2016

(86) PCT No.: PCT/EP2016/079812
§ 371 (c)(1),
(2) Date: Jun. 15, 2018

(87) PCT Pub. No.: WO2017/102416
PCT Pub. Date: Jun. 22, 2017

(65) Prior Publication Data
US 2020/0289043 A1     Sep. 17, 2020

(30) Foreign Application Priority Data

Dec. 17, 2015 (EP) ..................................... 15200809

(51) Int. Cl.
*H05B 33/08* (2020.01)
*H05B 47/125* (2020.01)
(Continued)

(52) U.S. Cl.
CPC ........... *H05B 47/125* (2020.01); *A61B 5/165* (2013.01); *G06F 1/163* (2013.01)

(58) Field of Classification Search
CPC ......... A61B 5/165; G06F 1/163; H05B 47/19; H05B 47/105
See application file for complete search history.

(56) References Cited

U.S. PATENT DOCUMENTS

2009/0262189 A1   10/2009  Marman
2012/0153828 A1   6/2012   Gordin
(Continued)

FOREIGN PATENT DOCUMENTS

CN   102802301 A   11/2012
CN   103348774 A   10/2013
(Continued)

*Primary Examiner* — Kurtis R Bahr
(74) *Attorney, Agent, or Firm* — Daniel J. Piotrowski

(57) ABSTRACT

A lighting system has a controller which receives input information from physiological sensors associated with users in the area illuminated by the lighting system. Anxiety is detected of a user or users when in or approaching a particular region of the area, and the lighting is changed to reduce the anxiety. In this way, lighting changes only need to be made when there is a need based on the response of the particular users. The system thus 5 enables energy savings as well as more stable lighting conditions.

14 Claims, 2 Drawing Sheets

(51) Int. Cl.
*A61B 5/16* (2006.01)
*G06F 1/16* (2006.01)

(56) References Cited

U.S. PATENT DOCUMENTS

| | | | |
|---|---|---|---|
| 2013/0249410 A1* | 9/2013 | Thompson | H05B 47/105 |
| | | | 315/158 |
| 2014/0285113 A1* | 9/2014 | Huang | H05B 47/19 |
| | | | 315/297 |
| 2014/0286517 A1 | 9/2014 | Luna et al. | |
| 2014/0327515 A1 | 11/2014 | Luna et al. | |
| 2015/0002292 A1* | 1/2015 | Cavalcanti | G08B 21/0275 |
| | | | 340/539.12 |
| 2017/0223807 A1* | 8/2017 | Recker | H02J 7/34 |

FOREIGN PATENT DOCUMENTS

| | | |
|---|---|---|
| EP | 2645823 A1 | 10/2013 |
| JP | 454599282 B2 | 1/2003 |

\* cited by examiner

LIGHTING SYSTEM AND A LIGHTING METHOD

CROSS-REFERENCE TO PRIOR APPLICATIONS

This application is the U.S. National Phase application under 35 U.S.C. § 371 of International Application No. PCT/EP2016/079812, filed on Dec. 6, 2016 which claims the benefit of European Patent Application No. 15200809.0, filed on Dec. 17, 2017. These applications are hereby incorporated by reference herein.

FIELD OF THE INVENTION

This invention relates to a lighting system and a lighting method, and a computer program. In particular, it relates to a lighting system which covers a large overall area through which users can move, and thereby enter different regions illuminated by different lights of the system.

BACKGROUND OF THE INVENTION

This invention relates to lighting systems which cover large areas. One main example is outdoor lighting systems, for example comprising a network of street lights or public space lights, for example in parks or other areas.

During darkness, outdoor spaces can often create feelings of danger or anxiety in pedestrians within the area, even when there is a lighting system which is turned on. Using a higher illuminance level can decrease this feeling of anxiety, but this of course gives rise to increased, and likely unacceptable, energy costs as well as unacceptable light pollution.

A solution to balance outdoor safety and energy savings is to use presence detection, whereby a light is set to a higher level if a person is present. However, this will lead to a large amount of unnecessary switching of light levels, which gives a restless character to the area, which is not appreciated by occupants of the area.

There is therefore a need for a lighting system which adapts according to the needs of users in the area illuminated by the lighting system while also enabling wasting of energy to be reduced.

SUMMARY OF THE INVENTION

The invention is defined by the claims.

According to examples in accordance with an aspect of the invention, there is provided a lighting system comprising:

an outdoor street and/or public space light for illuminating an area;

a set of physiological sensors for detecting anxiety to be worn or carried by users when in the area; and a controller for controlling the lighting system, comprising:

an input for receiving input information from the set of physiological sensors associated with users in the area illuminated by the lighting system and for receiving information about the location of the users within the area; and an output for controlling the outdoor street and/or public space light of the lighting system, wherein the controller is adapted to:

determine, from the input information, anxiety of the user or users when in or approaching a particular region of the area; and alter the output in an attempt to reduce the anxiety.

Next to the set of physiological sensors, in addition physical sensors may be provided.

This controller controls a lighting system in a way which aims to reduce anxiety of users present in the area illuminated by the system. In this way, lighting changes only need to be made when there is a need based on the behavior of the particular users. For a person who experiences no anxiety in dim lighting conditions, energy can be saved (compared to a presence based system) and changes to the light setting can be avoided, giving a more calm general illumination.

Lighting settings, such as lighting level and/or color temperature, are changed only when people passing by experience the space as unsafe. This approach provides an improved balance between reducing the feeling of anxiety for pedestrians and making energy savings. At the same time, light pollution may be reduced by avoiding constantly high light levels or unnecessary switching due to simple presence detection.

The anxiety is determined based on a measured personal feeling of danger, rather than generic risk detection based on infrared cameras. This also means anxiety can be taken into account, even when no other detectable risk factor is present.

The invention is of particular interest in regions where there is darkness for many of the normal waking hours, for example in Nordic areas where people may avoid going outside because there are only a few hours of daylight during the winter period.

In an embodiment, the lighting system according to the invention is provided, wherein the outdoor street and/or public space light is comprised within a network of outdoor street and/or public space lights. Such a network may be advantagous because it may cover a larger area comprising multiple regions for which more elaborate and individual control is possible.

The controller may be adapted to:

alter the output to control at least one light which illuminates the region in which the user is present; and/or alter the output to control at least one light which illuminates the region which the user is approaching; and/or alter the output to control at least one light which illuminates a region in the vicinity of the user.

The lighting may be controlled for a region in which the user is present, or a region they are about to enter based on raised anxiety in anticipation of entering a particular area. By tracking the position of a user, it is possible to predict where they are heading. An alternative is to control the lighting around the user (as well or instead of the actual region in which they are located) so that they can see further around them more clearly, and possibly also be seen less clearly by others.

The controller may be adapted to report anxiety information to a lighting system administrator or safety body.

In this way, information relating to detected feelings of danger can be shared with the lighting system administrator, which can then increase the default light levels of particular areas. In this way, it is possible to analyze which regions structurally cause more unsafe feelings, so that these places can be adjusted and made more safe. The information can also be shared with police or other safety bodies via the lighting system.

As mentioned before, the lighting system may comprise a network of outdoor street and/or public space lights. The lights thus cover large areas through which people move. However, the invention may also be employed in large indoor buildings, again when it is desired not to keep all lights on to a high intensity during darkness hours. In the same way as for an outdoor system, energy savings may be made by having a dimmer light setting, and only increasing brightness when needed by the users.

The set of physiological sensors may comprise one or more of:
a galvanic skin response sensor;
a heart rate sensor;
a blood pressure sensor;
a sensor measuring pupil size;
a bio-sensor measuring cortisone and/or testosterone levels;
a respiratory rate sensor;
an electrodermal activity sensor;
and alternatively, in an embodiment, additional physical sensors may be provided, said physical sensors may comprise one or more of:
a motion sensor;
a sensor for detecting the motion of the head of a user relative to their body.

The sensors may be wearables, for example for detecting bio-signals such as heart rate and GSR (galvanic skin response), to detect increased levels of anxiety. The sensors can also detect if people watch more over their shoulders, or start walking faster or follow any other motion pattern that can be induced by a feeling of danger.

Electrodermal (response) activity sensor may for example comprise a skin conductance sensor such as skin conductance response (SCR), psychogalvanic reflex sensor (PGR), sympathetic skin response sensor (SSR) and skin conductance level sensor (SCL).

The controller is for example adapted to determine increases in galvanic skin response and/or heart rate from a baseline as an indicator of anxiety. In this way, the system detects increases in anxiety associated with certain regions illuminated by the lighting system. The system then calibrates to the general physiological signals of the users. Hence, in an embodiment, the controller is adapted to calibrate the system to physiological signals of multiple users within the area.

Further, in an embodiment, the received information about the location of the users within the area is based on a detection of coded light output.

Examples in accordance with another aspect of the invention provide a method for controlling a lighting system, comprising controlling an outdoor street and/or public space light, the method comprising:
receiving input information from physiological sensors for detecting anxiety associated with users in the area illuminated by the lighting system;
receiving information about the location of the users within the area; and
determining, from the input information, anxiety of a user or users when in or approaching a particular region of the area; and
controlling the lighting system in an attempt to reduce the anxiety.

This method controls a lighting system in dependence on detected anxiety of users within the illuminated area.

The method may comprise:
controlling a light which illuminates the area in which a user is present; and/or
controlling a light which illuminates an area which a user is approaching; and/or
controlling one or more lights which illuminate an area or areas in the vicinity of a user.

Different changes to the light settings may be appropriate for different detected sensor signals.

The method may comprise reporting anxiety information to a lighting system administrator or safety body. This can be used to enable the lighting (or even the design of the space beyond only the lighting) for a particular region to be redesigned if it shows frequent anxiety of users.

Controlling the lighting system may comprise altering a brightness level and/or an output color and/or a beam shape of one or more lights. Thus, there are different ways to adapt the lighting to reduce the anxiety levels experienced.

The method may comprise detecting increases in galvanic skin response and/or heart rate from a baseline as an indicator of anxiety.

In an embodiment of the method, the received information about the location of the users within the area is based on a detection of coded light output from a network of outdoor street and/or public space lights. The method may be implemented in software.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a lighting system with a controller which receives input information from physiological sensors associated with users in the area illuminated by the lighting system. Anxiety is detected of a user or users when in or approaching a particular region of the area, and the lighting is changed to reduce the anxiety. In this way, lighting changes only need to be made when there is a need based on the characteristics of the particular users. The system thus enables energy savings as well as more stable lighting conditions.

Figure 1:
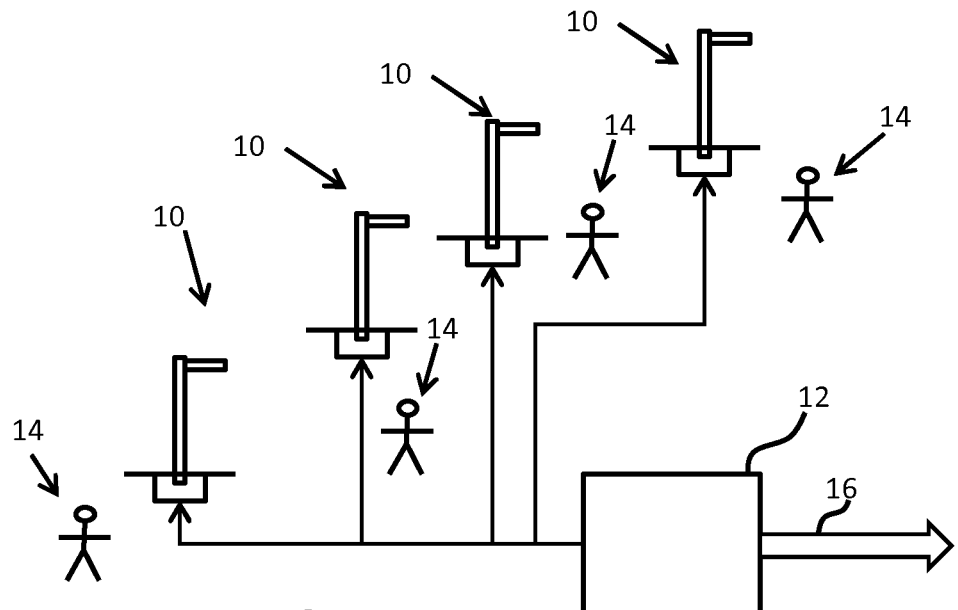
FIG. 1 shows a lighting system.

FIG. 1 shows a lighting system comprising a set of lights 10 for illuminating an area. Here, the outdoor street and/or public space light according to the first aspect of the invention is comprised within a network of outdoor street and/or public space lights 10. The lights form a network.

The lights 10 are all shown as light poles. However, the network may include wall mounted lights, ground mounted lights, or lights mounted on other structures such as bridges and tunnels.

The network of lighting units may include hundreds of thousands of devices. For instance, the number of lighting units in a city like Los Angeles or Buenos Aires is tens of thousands of devices. In such a case, the lights are controlled in groups, forming sub-networks.

The lights may include indoor lights as well, or the system may be an indoor system, although the invention is of interest for large spaces where there is movement of people between regions which are illuminated by different lights.

The lights 10 are controlled by a controller 12.

People 14 move around in the area illuminated by the lighting system.

The users 14 carry or wear a set of physiological sensors and these relay sensor data to the controller 12.

The sensor data may be sent directly to the controller 12 for example over a wireless internet connection. Alternatively, the sensor data may be communicated to a nearby light 10 which then relays the information to the controller 12.

The communication between the lights 10 and the controller 12 may be wired or wireless.

There already exist networked street lighting solutions. The network for example enables online determination of how much energy street lights are using and which ones need repair. Full control is enabled of the lighting provided, for example enabling schedules and dimming levels to be set on demand. One such solution is the CityTouch® product of Philips®. It provides simple a web application to manage street lights remotely and analyze lighting data including energy usage and luminaire status.

Each luminaire includes a central processing unit (CPU), and a communications module (e.g., using the General Packet Radio Service, GPRS), as well as a positioning module such as a GPS module. The GPS module is used to provide location information, for example for auto-commissioning and auto-locating.

The system of this invention may be provided as an add-on to such existing lighting network systems.

Figure 2:
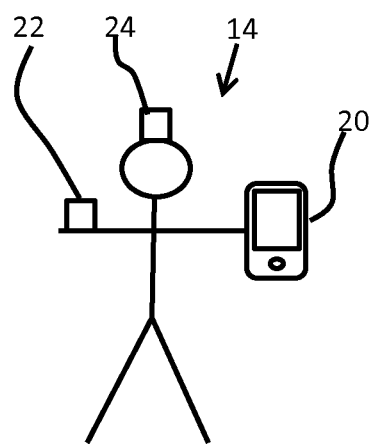
FIG. 2 shows a user wearing and carrying various sensors for providing information to the lighting system controller.

FIG. 2 shows a user 14 wearing and carrying a set of sensors.

A first sensor 20 is for identifying the location of the user. This may for example comprises a GPS system of a mobile phone of the user. The first sensor may make use of global, regional or local positioning data received from, for example, a satellite. The US government maintained Global Positioning System (GPS) is a collection of satellites each providing a wireless signal. Other examples are the Russian GLONASS satellite system, the European Galileo satellite system, the Chinese Beidou and COMPASS satellite systems, the Indian IRNSS satellite system and the Japanese QZSS satellite system.

The first sensor may instead make use of the lighting system, for example based on the detection of coded light output from the lights. Alternatively, the lighting system may detect the location of the user based on detection of radio frequency (RF) signals from wearable devices of the user, such as signal strengths and time of flight.

A second sensor comprises a galvanic skin response (GSR) sensor. A threshold is then applied to the GSR measurement to provide an indication of the anxiety level. There are various possible approaches for setting the threshold.

A user may for example wear the GSR sensor daily, and this allows an estimate to be made of a general baseline level, e.g. the minimum value encountered or the 5th percentile score (to exclude very low values like meditation). A threshold for that user can then be set as a certain percentage above this baseline value.

A histogram of all values encountered during the last days or weeks may be formed. A threshold can then directly be derived as the 70th percentile value, or the 90th percentile value. GSR measurements above this threshold are interpreted as an arousal which may be brought about by fear or anxiety.

Using historical data, it is possible to estimate the GSR levels of the user when usually in the area concerned during day time hours. A threshold can then be set for example as 140% or 150% of this value. In order for this threshold approach to be possible, the user will need to have been in this area during day time hours at least once.

It is also possible to make an estimate of the GSR levels associated with the same form of locomotion, e.g. cycling or walking during day time hours. The threshold could then depend on the activity currently performed by the user, for instance a certain percentage above this value. Again, in order for this threshold approach to be available, the user will need to have performed the activity (cycling, running or walking) during day time hours at least once.

All of the above threshold calculations may be absolute in the sense that they do not take into account which GSR levels the user had immediately before approaching the area under consideration. Instead, relative threshold calculations may be performed, basically looking at the change in GSR level when approaching or when in the area under consideration, for instance the change in the last 5 or 20 seconds. If such an increase is above a certain increase-threshold this could lead to lighting adaptations as well.

The increase-threshold could be calculated in a similar way as the absolute thresholds above, based on GSR increases usually present during the day, or based on increases present while previously approaching this area in daylight or based on increases usually present doing the same activity during daylight hours.

These concepts for setting thresholds may be applied to other physiological sensor signals and do not apply exclusively to GSR measurements. There may also be multiple thresholds (with different scores for different value ranges) or indeed analog values may be processed by the system in a more complicated decision algorithm.

A third sensor comprises a heart rate sensor. In the example shown, these are combined into a sensor device 22 worn on the wrist of the user. A fourth sensor comprises a motion sensor 24. The overall motion of the user (their direction, velocity and acceleration) may be detected, either based on GPS data or using accelerometers. However, the motion of individual body parts may also be detected using motion sensors, for example to detect if a person is repeatedly looking over their shoulder.

Together, the sensors form a set of physiological sensors. These sensors are for example wearables. The physiological sensors may be any suitable bio-sensor for measuring physiological signal which is an indicator of anxiety.

A physical sensor may be any sensor for measuring movement, velocity, acceleration. Other physical sensors may be used, for example measuring wind speed and temperature, which may also contribute to a feeling of anxiety (a cold windy night may give greater anxiety than a still warm night even with the same lighting conditions).

Heart rate and GSR (galvanic skin response) are known ways to detect increased levels of anxiety. People also tend to look more over their shoulders when anxious, or they may start walking faster or follow other detectable motion patterns. Thus, it is possible to use a combination of wearables, e.g. embedded in clothing, to detect various parameters, such as way of walking, posture, head rotation relative to body movement.

Since heart rate or GSR signals are raised in the case of anxiety, it is preferred that the current absolute measurement is calibrated based on a measurement for a known and safe feeling situation for that user. It is the heart rate increase, or the GSR increase, that indicates anxiety. This increase can be detected based on comparison with earlier measurements done by the same wearable sensor.

The increase also depends on how high the absolute bio-signal level was just before the anxiety feeling started. The indication of anxiety may also be corrected to take account of the initial reading as well as a general baseline.

In response to the sensor signals, the controller 12 changes the light output of the lights, typically by increasing the light levels of one or more of the lights of the network.

The color temperature, beam shape or any other light output parameter may also (or instead) be changed. The change in lighting is only needed when people passing by experience the space as unsafe. In one example, the light corresponding to the location of the user is changed, and optionally also lighting in neighboring regions. As another example, the light level may be increased in the regions surrounding the user but excluding the location of the user. This may increase the perceived safety without making the anxious person feel like a highlighted moving target.

Anxiety is often also anticipated, and will therefore be measurable in an increased bio-signal level even before the unsafe area is reached. In this way, the lighting system can increase light levels in anticipation of the user entering the corresponding region of the area.

Thus, the controller 12 is may determine, from the sensor information, anxiety of a user or users when in or else when approaching a particular region of the area. The change in lighting is to control a light which illuminates the area in which the user is present and/or to control a light which illuminates an area which the user is approaching and/or to control one or more lights which illuminate an area or areas in the vicinity of the user.

FIG. 1 shows that the controller 12 also provides an external output 16. This output 16 enables information to be shared with one or more third parties via the communication infrastructure of the street lighting system extremely high levels of anxiety could set warning signals/alarms to go off.

The system may also analyze which regions give structurally more unsafe feelings, so that these places can be adjusted in order to increase the feeling of safety for the pedestrians. The output 16 can be used for this purpose as well. The bio-signal data of multiple users can be analyzed and compared to derive general information about a particular region. As mentioned above, it is best to compare the increases in heart rate or GSR people. For this purpose, measurements may be taken of the heart rate or GSR of the same person but taken during the daytime, or taken at a safer (lighter) stretch of a public area at the same time of day.

The data collected by a sensor may be interpreted by a microcontroller of the sensor. It is also possible, for cost savings in respect of the wearable device, that the collected data is transmitted to a remote device, such as the smartphone 20 or even the controller 12. The smartphone or the controller 12 may then have more processing power to run software for the data analysis.

The number of events (i.e. detected anxiety occurrences) that are registered per region may be monitored continuously by a service provider. If a high level of anxiety is detected, or when groups of people with similar feelings are detected, it is also possible that the police are automatically warned in real time.

Data analysis of collected data during longer periods of time can be used to improve local areas that have a strong correlation with feelings of danger. This may involve changing the light settings or redesigning the lighting or even other aspects of the design of the space.

For example, the system may provide a service to city administrators (e.g. planning authorities). Detected perceived general levels of danger are shared with a city authority by the output 16 of FIG. 1, and this authority can then take action to improve the safety of the troubled spaces throughout the city.

When sensors are used which enable the position of the head to be determined, the system may adjust lighting based on this information.

Measurement of the rotation of the head relative to the movement of the body is an indication of feeling unsafe. If a user looks around their shoulder frequently, the user may feel unsafe. If this is correlated with a change in bio-signals and speed of motion (accelerating), the combined data will make the determination of the feeling of anxiety more robust.

The head orientation information in combination with the other bio-sensor data of all users may be gathered and analyzed to determine the lighting intensity for specific areas. For example, in areas where people feel safe the light intensity can be lowered to save energy.

The system may be used in combination with other smart systems to change the light level in the street based on need, such as camera based systems that can detect potential risks based on irregular behavior by pedestrians.

Another option is for the system to measure the distance changes between people. This provides a way to analyze if people are avoiding other people. This also could be an indicator of unsafe feelings. In such a case, lighting conditions could also take into account the location of multiple people or groups of people. This can be achieved by localizing the pedestrians with respect to lamp posts via camera based or RF signal strength based triangulation.

Figure 3:
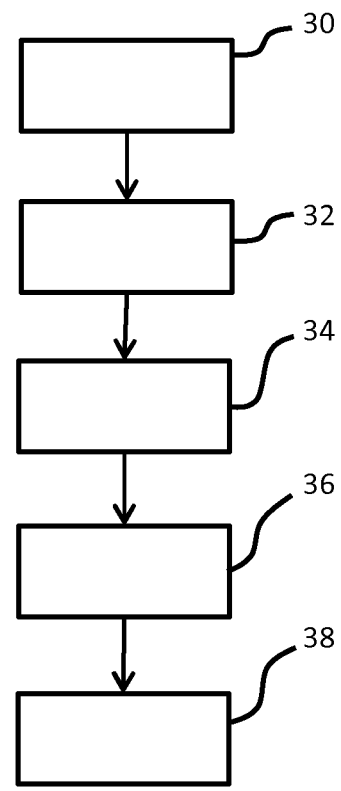
FIG. 3 shows a lighting method.

FIG. 3 shows a method for controlling a lighting system, as implemented by a lighting controller.

In step 30 input information is received from physiological sensors associated with users in the area illuminated by the lighting system.

In step 32 information is received about the location of the users within the area.

From the input information, the anxiety of a user or users is determined in step 34 when in or approaching a particular region of the area. This anxiety is then associated with that particular area.

In step 36, the lighting system is controlled in an attempt to reduce the anxiety. In the most basic form, this involves increasing the light level in that particular region.

However it may be more sophisticated. For example, the control may be of light which illuminates the area in which a user is present, or of a light which illuminates an area which a user is approaching or one or more lights which illuminate an area or areas in the vicinity of a user.

The method optionally includes reporting anxiety information to a lighting system administrator or safety body in step 38. The reporting may be performed when multiple users experience anxiety at the same location at the same or different times.

Figure 4:
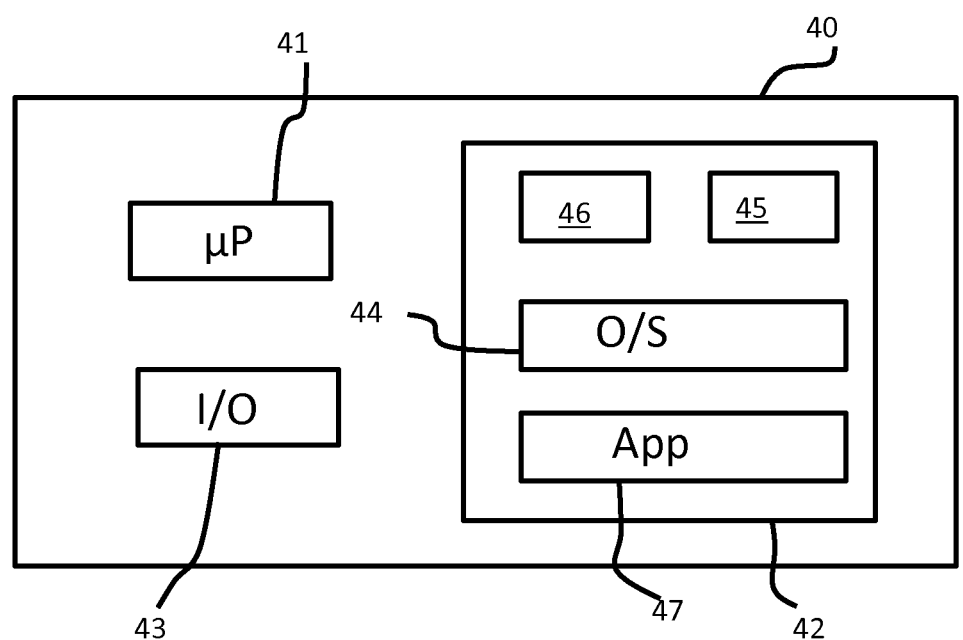
FIG. 4 shows a computer for implementing the method.

As discussed above, the invention makes use of a controller for processing the sensor data. Some data processing may be carried out at the sensor or else it may all be central. FIG. 4 illustrates an example of a computer 40 for implementing controller described above.

The computer 40 includes, but is not limited to, PCs, workstations, laptops, PDAs, palm devices, servers, storages, and the like. Generally, in terms of hardware architecture, the computer 40 may include one or more processors 41, memory 42, and one or more I/O devices 43 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 41 is a hardware device for executing software that can be stored in the memory 42. The processor 41 can be virtually any custom made or commercially available processor, a central processing unit (CPU), a digital signal processor (DSP), or an auxiliary processor among several processors associated with the computer 40, and the processor 41 may be a semiconductor based microprocessor (in the form of a microchip) or a microprocessor.

The memory 42 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 42 may incorporate electronic, magnetic, optical, and/or other types of storage media. Note that the memory 42 can have a distributed architecture, where various components are situated remote from one another, but can be accessed by the processor 41.

The software in the memory 42 may include one or more separate programs, each of which comprises an ordered listing of executable instructions for implementing logical functions. The software in the memory 42 includes a suitable operating system (O/S) 44, compiler 45, source code 46, and one or more applications 47 in accordance with exemplary embodiments.

The application 47 comprises numerous functional components such as computational units, logic, functional units, processes, operations, virtual entities, and/or modules.

The operating system 44 controls the execution of computer programs, and provides scheduling, input-output control, file and data management, memory management, and communication control and related services.

Application 47 may be a source program, executable program (object code), script, or any other entity comprising a set of instructions to be performed. When a source program, then the program is usually translated via a compiler (such as the compiler 45), assembler, interpreter, or the like, which may or may not be included within the memory 42, so as to operate properly in connection with the operating system 44. Furthermore, the application 47 can be written as an object oriented programming language, which has classes of data and methods, or a procedure programming language, which has routines, subroutines, and/or functions, for example but not limited to, C, C++,C#, Pascal, BASIC, API calls, HTML, XHTML, XML, ASP scripts, JavaScript, FORTRAN, COBOL, Perl, Java, ADA, .NET, and the like.

The I/O devices 43 may include input devices such as, for example but not limited to, a mouse, keyboard, scanner, microphone, camera, etc. Furthermore, the I/O devices 47 may also include output devices, for example but not limited to a printer, display, etc. Finally, the I/O devices 43 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 43 also include components for communicating over various networks, such as the Internet or intranet.

When the computer 40 is in operation, the processor 41 is configured to execute software stored within the memory 42, to communicate data to and from the memory 42, and to generally control operations of the computer 40 pursuant to the software. The application 47 and the operating system 44 are read, in whole or in part, by the processor 41, perhaps buffered within the processor 41, and then executed.

When the application 47 is implemented in software it should be noted that the application 47 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The invention is of particular interest for outdoor safety. However, it may be used in indoor spaces, such as hospitals and mental institutions, to detect locations or situations where people feel unsafe or anxious, and warn supervising persons and create comforting light for example by using colored light.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A lighting system comprising:
an outdoor street and/or public space light for illuminating an area;
a set of physiological sensors for detecting anxiety to be worn or carried by users when in the area; and
a controller for controlling the lighting system, comprising:
an input for receiving input information from the set of physiological sensors associated with users in the area illuminated by the lighting system and for receiving information about the location of the users within the area; and
an output for controlling the outdoor street and/or public space light of the lighting system, wherein the controller is adapted to:
determine, from the input information, anxiety of the user or users when in or approaching a particular region of the area; and
alter the output in an attempt to reduce the anxiety, wherein the controller is adapted to calibrate the system to physiological signals of multiple users within the area.

2. The lighting system as claimed in claim 1, wherein the outdoor street and/or public space light is comprised within a network of outdoor street and/or public space lights.

3. The lighting system as claimed in claim 1, wherein the set of physiological sensors comprise one or more of:
a galvanic skin response sensor;
a heart rate sensor;
a blood pressure sensor;
a sensor measuring pupil size;
a bio-sensor measuring cortisone and/or testosterone levels;
a respiratory rate sensor;
an electrodermal activity sensor.

4. The lighting system as claimed in claim 3, wherein the controller is adapted to determine increases in galvanic skin response and/or heart rate from a baseline as an indicator of anxiety.

5. The lighting system as claimed in claim 1, wherein the set of physiological sensors comprise wearable sensors.

6. A lighting system comprising:
an outdoor street and/or public space light for illuminating an area;
a set of physiological sensors for detecting anxiety to be worn or carried by users when in the area; and
a controller for controlling the lighting system, comprising:
an input for receiving input information from the set of physiological sensors associated with users in the area illuminated by the lighting system and for receiving information about the location of the users within the area; and
an output for controlling the outdoor street and/or public space light of the lighting system, wherein the controller is adapted to:
determine, from the input information, anxiety of the user or users when in or approaching a particular region of the area; and
alter the output in an attempt to reduce the anxiety, wherein the received information about the location of the users within the area is based on a detection of coded light output.

7. The lighting system as claimed in claim 6, wherein the controller is further adapted to:
alter the output to control at least one light which illuminates the particular region in which the user is present; and/or
alter the output to control at least one light which illuminates the particular region which the user is approaching; and/or
alter the output to control at least one light which illuminates a region in the vicinity of the user.

8. A method for controlling a lighting system comprising controlling an outdoor street and/or public space light, the method comprising:
receiving input information from physiological sensors for detecting anxiety associated with users in the area illuminated by the lighting system;
receiving information about the location of the users within the area;
determining, from the input information, anxiety of a user or users when in or approaching a particular region of the area;
controlling the lighting system in an attempt to reduce the anxiety; and
wherein the controlling includes calibrating the system to physiological signals of multiple users within the area.

9. The method as claimed in claim 8, comprising:
controlling a light which illuminates the particular region in which a user is present; and/or
controlling a light which illuminates the particular region which a user is approaching; and/or
controlling a light which illuminate a region in the vicinity of a user.

10. The A method as claimed in claim 8, further comprising reporting anxiety information to a lighting system administrator or safety body.

11. The method as claimed in claim 8, wherein controlling the lighting system comprises altering a brightness level and/or an output color and/or a beam shape of one or more lights.

12. The method as claimed in claim 8, comprising detecting increases in galvanic skin response and/or heart rate from a baseline as an indicator of anxiety.

13. A method for controlling a lighting system comprising controlling an outdoor street and/or public space light, the method comprising:
receiving input information from physiological sensors for detecting anxiety associated with users in the area illuminated by the lighting system;
receiving information about the location of the users within the area; and
determining, from the input information, anxiety of a user or users when in or approaching a particular region of the area; and
controlling the lighting system in an attempt to reduce the anxiety, wherein the received information about the location of the users within the area is based on a detection of coded light output from a network of outdoor street and/or public space lights.

14. A non-transitory computer readable medium having instructions adapted program comprising code means adapted to perform the method of claim 8 when said instruction are ran on a computer.

* * * * *